United States Patent
Nomi

(10) Patent No.: US 12,313,906 B2
(45) Date of Patent: May 27, 2025

(54) OBJECTIVE OPTICAL SYSTEM, IMAGE PICKUP APPARATUS, AND ENDOSCOPE

(71) Applicant: OLYMPUS CORPORATION, Hachioji (JP)

(72) Inventor: Motoko Nomi, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 511 days.

(21) Appl. No.: 17/876,329

(22) Filed: Jul. 28, 2022

(65) Prior Publication Data

US 2022/0365315 A1  Nov. 17, 2022

Related U.S. Application Data

(63) Continuation of application No. PCT/JP2020/005998, filed on Feb. 17, 2020.

(51) Int. Cl.
| | |
|---|---|
| *G02B 9/10* | (2006.01) |
| *A61B 1/00* | (2006.01) |
| *A61B 1/04* | (2006.01) |
| *G02B 23/24* | (2006.01) |

(52) U.S. Cl.
CPC ............ *G02B 9/10* (2013.01); *A61B 1/00188* (2013.01); *G02B 23/243* (2013.01); *A61B 1/04* (2013.01); *G02B 23/2484* (2013.01)

(58) Field of Classification Search
None
See application file for complete search history.

(56) References Cited

U.S. PATENT DOCUMENTS

| | | |
|---|---|---|
| 8,587,876 B2 | 11/2013 | Katayose et al. |
| 8,810,917 B2 | 8/2014 | Katayose et al. |
| 9,213,171 B2 | 12/2015 | Katayose et al. |
| 9,933,610 B2 | 4/2018 | Takasugi |
| 2012/0120501 A1* | 5/2012 | Katayose ....... G02B 15/143507 359/689 |

(Continued)

FOREIGN PATENT DOCUMENTS

| | | |
|---|---|---|
| JP | 10980344 A | 3/1997 |
| JP | H0980344 A * | 3/1997 |

(Continued)

OTHER PUBLICATIONS

International Preliminary Report on Patentability (IPRP) (and English language translation thereof) dated Sep. 1, 2022, issued in International Application No. PCT/JP2020/005998.

(Continued)

*Primary Examiner* — Shan Liu
(74) *Attorney, Agent, or Firm* — Holtz, Holtz & Volek PC

(57) ABSTRACT

There is provided an objective optical system, an image pickup apparatus, and an endoscope that are small in size and easy to assemble. The objective optical system includes, in order from the object side to the image side, a negative front lens group, an aperture stop, and a positive rear lens group. The front lens group includes a negative first lens disposed closest to the object, a meniscus second lens having a convex surface facing toward the image side, and a view-direction changing element. The objective optical system satisfies the following conditional expressions (1) to (4):

$$9<FL2/FL<15 \qquad (1)$$

$$0.3<FL1/FLf<0.64 \qquad (2)$$

$$-95<(r2f+r2r)/(r2f-r2r)<-18 \qquad (3)$$

$$2.8<FLr/FL<4 \qquad (4).$$

6 Claims, 6 Drawing Sheets

(56) References Cited

U.S. PATENT DOCUMENTS

| | | | |
|---|---|---|---|
| 2014/0043521 A1 | 2/2014 | Katayose et al. | |
| 2014/0320703 A1 | 10/2014 | Katayose et al. | |
| 2018/0017777 A1* | 1/2018 | Takasugi | G02B 5/04 |
| 2020/0341262 A1* | 10/2020 | Inoue | G02B 23/243 |

FOREIGN PATENT DOCUMENTS

| | | |
|---|---|---|
| JP | 2012108278 A | 6/2012 |
| JP | 6173648 B1 | 7/2017 |
| WO | 2017104268 A1 | 6/2017 |

OTHER PUBLICATIONS

International Search Report (ISR) (and English translation thereof) dated Apr. 7, 2020, issued in International Application No. PCT/JP2020/005998.

Written Opinion dated Apr. 7, 2020, issued in International Application No. PCT/JP2020/005998.

\* cited by examiner g 435.84nm
F 486.13nm
d 587.56nm
C 656.27nm

OBJECTIVE OPTICAL SYSTEM, IMAGE PICKUP APPARATUS, AND ENDOSCOPE

CROSS REFERENCES TO RELATED APPLICATION

The present application is a continuation application of PCT/JP2020/005998 filed on Feb. 17, 2020; the entire contents of which are incorporated herein by reference.

BACKGROUND OF INVENTION

Technical Field

The present invention relates to an objective optical system, an image pickup apparatus, and an endoscope.

Description of the Related Art

One type of an objective optical system for use in an endoscope is an oblique-view objective optical system. The oblique-view objective optical system is used in forward view, side view, or backward view.

Conventional oblique-view objective optical system uses an optical path changing element having a long glass path length provided in the optical system. An example of the optical path changing element having a long optical path length is a prism. Hence oblique-view objective optical systems need a large space in which the prism is provided.

Due to the need to provide a large space, the entire length of oblique-view objective optical systems tends to be longer than that of direct-view objective optical systems. In consequence, oblique-view objective optical systems tend to be larger in size than direct-view objective optical systems. Therefore, downsizing of oblique-view objective optical systems is particularly desired.

Japanese Patent No. 6173648 discloses a single focal length objective optical system including a prism. This objective optical system includes a negative front lens group, a positive rear lens group, and a prism arranged between them.

SUMMARY OF THE INVENTION

To solve the above problem and to achieve the object, an objective optical system according to at least some embodiments of the present invention comprises, in order from the object side to the image side:
  a negative front lens group;
  an aperture stop; and
  a positive rear lens group,
wherein the front lens group includes a negative first lens disposed closest to the object, a meniscus second lens having a convex surface facing toward the image side, and a view-direction changing element, and the objective optical system satisfies the following conditional expressions (1) and (2):

$$9 < FL2/FL < 15 \quad (1)$$

$$0.3 < FL1/FLf < 0.64 \quad (2)$$

$$-95 < (r2f + r2r)/(r2f - r2r) < -18 \quad (3)$$

$$2.8 < FLr/FL < 4 \quad (4)$$

where FL1 is the focal length of the first lens, FL2 is the focal length of the meniscus second lens, FLf is the focal length of the front lens group, and FL is the focal length of the entire objective optical system, r2f is the curvature radius of the object side surface of the meniscus second lens, r2r is the curvature radius of the image side surface of the meniscus second lens, and FLr is the focal length of the rear lens group.

In another aspect, there is also provided an image pickup apparatus. An image pickup apparatus according to at least some embodiments of the present invention comprises the objective optical system described above and an image pickup element.

In another aspect, there is also provided an endoscope. An endoscope according to at least some embodiments of the present invention comprises the objective optical system described above and an image pickup element.

DETAILED DESCRIPTION OF THE INVENTION

Prior to description of examples of the present invention, the operation and advantageous effects of embodiments according to certain modes of the present invention will be described. To describe the operation and advantageous effects of the embodiments specifically, specific exemplary modes will be given. However, the exemplary modes and examples that will be described later constitute only a portion of the modes encompassed by the present invention, which include many variations. Therefore, it should be understood that the present invention is not limited by the exemplary modes.

Figure 1A:
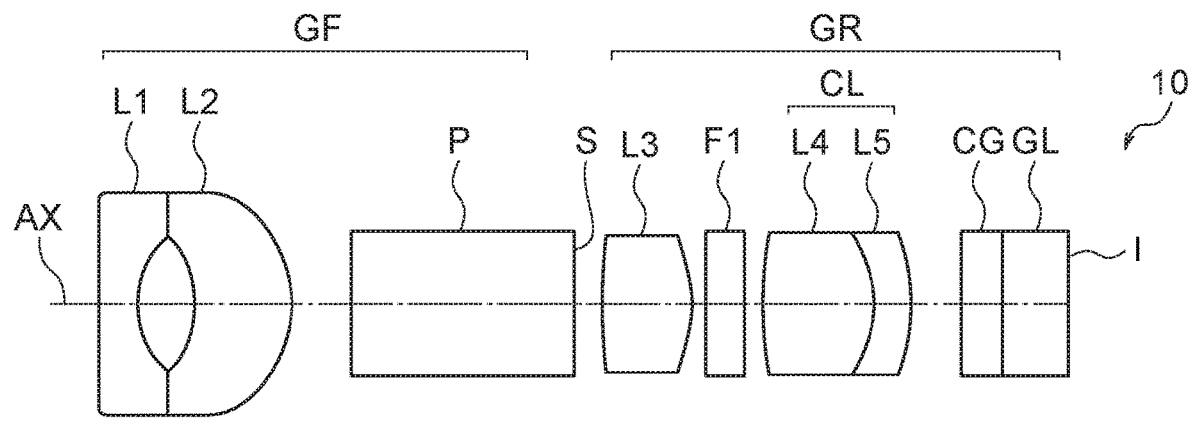
FIG. 1A is a cross sectional view of the lenses in an objective optical system according to a first embodiment.
Figure 1B:
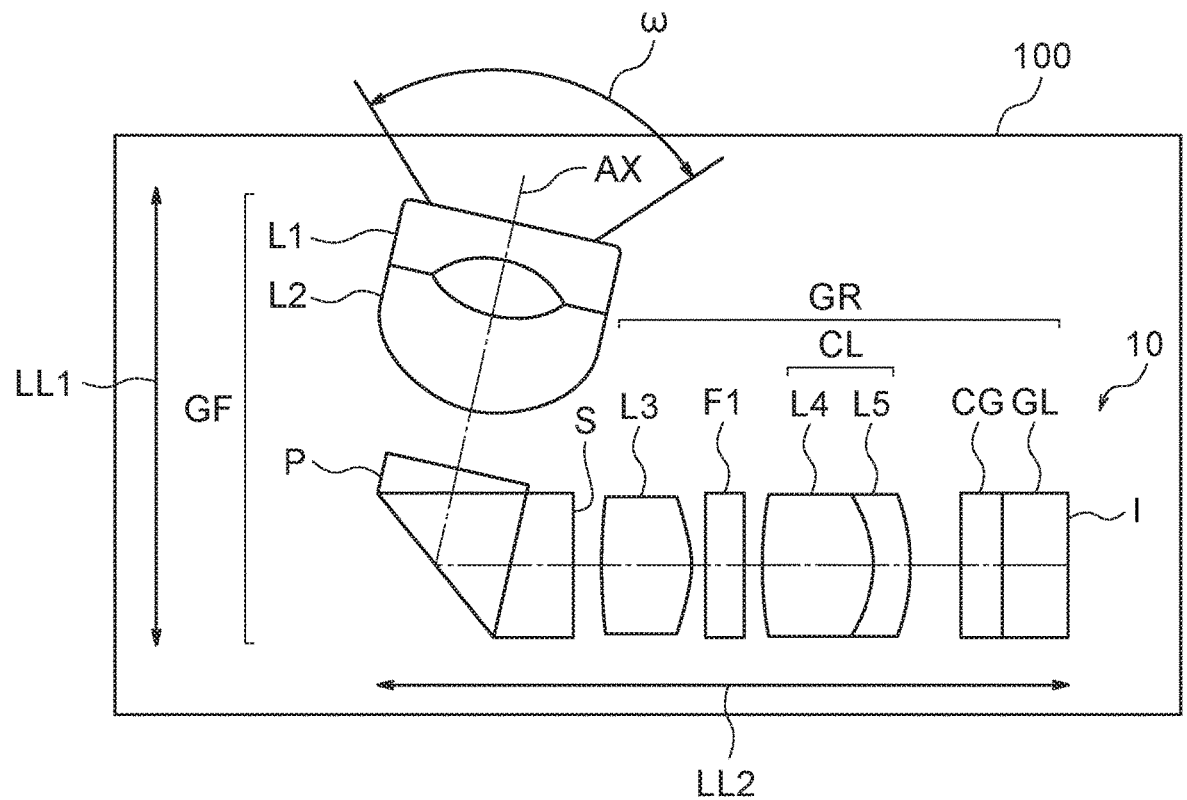
FIG. 1B is a cross sectional view of the lenses in the objective optical system according to the first embodiment, of which the direction of view is bent.

FIG. 1A is a cross sectional view of the lenses in an objective optical system 10 according to the first embodiment. FIG. 1B is a cross sectional view of the lenses in the objective optical system 10 according to the embodiment, of which the direction of view is bent. The objective optical system 10 according to the embodiment is suitable for use in an oblique-view endoscope 100. In FIG. 1B, what is denoted by c) is the angle of view.

An objective optical system 10 includes, in order from the object side to the image side, a negative front lens group GF, an aperture stop S, and a positive rear lens group GR. The front lens group GF includes a negative first lens L1 on the object side, a meniscus second lens L2 having a convex surface facing toward the image side, and a view-direction changing element P. The objective optical system 10 satisfies the following conditional expressions (1) and (2):

$$9 < FL2/FL < 15 \tag{1}$$

$$0.3 < FL1/FLf < 0.64 \tag{2}$$

where FL1 is the focal length of the first lens L1, FL2 is the focal length of the meniscus second lens L2, FLf is the focal length of the front lens group GF, and FL is the focal length of the entire objective optical system 10.

The objective optical system of this embodiment includes a negative front lens group GF. Thus, the objective optical system 10 is a retro-focus optical system, in which a space that allows focus adjustment during assembly can be provided.

The first lens L1 is a negative lens and the meniscus second lens L2 is a positive meniscus lens. This design can make the ray height low while providing a space for arranging the lenses in the front lens group GF and the view-direction changing element P, so that downsizing of the optical system can be achieved. The view-direction changing element P is arranged on the image side in the negative front lens group GF. Moreover, the aperture stop S and the positive rear lens group GR are arranged subsequently to the front lens group GF. In consequence, the ray height is not too high in the region after the front lens group GF. Hence, downsizing of the optical system can be achieved.

The aperture stop S is arranged between the negative front lens group GF and the positive rear lens group GR.

The downsizing of the optical system includes two aspects, that is downsizing with respect to the radial direction and downsizing with respect to the direction along the optical axis. In the case of an endoscope 100 shown in FIG. 1B, downsizing with respect to the radial direction means reduction in the length LL1 of the diameter of the bent objective optical system 10. In the same case, downsizing with respect to the direction along the optical axis means reduction in the longitudinal length LL2 of the objective optical system 10.

The view-direction changing element P is a prism that is shaped in such a way as to bend the optical axis AX. The view-direction changing element can change the direction of view of the observer.

Conditional expression (1) defines an appropriate range of the ratio of the focal length of the meniscus second lens L2 and the focal length of the entire objective optical system 10. Satisfying conditional expression (1) is contributive to downsizing with respect to the radial direction of the objective optical system 10.

If the value of FL2/FL exceeds the upper limit value of conditional expression (1), the refractive power of the meniscus second lens L2 is too low. Then, the ray height in the region after the meniscus second lens L2 tends to be high.

Consequently, a space for the lenses and the view-direction changing element P cannot be provided. Moreover, distortion and chromatic aberration of magnification generated by the first lens L1 cannot be corrected sufficiently.

If the value of FL2/FL falls below the lower limit value of conditional expression (1), the refractive power of the meniscus second lens L2 is too high. The high refractive power of the meniscus second lens L2 will break the balance of the retro focus configuration. In consequence, a sufficient space for focus adjustment cannot be left.

Conditional expression (2) defines an appropriate range of the ratio of the focal length of the first lens L1 and the focal length of the negative front lens group GF. Satisfying conditional expression (2) is contributive to downsizing of the objective optical system 10 with respect to the radial direction.

If the value of FL1/FLf exceeds the upper limit value of conditional expression (2), the refractive power of the first lens L1 is too low. Then, the ray height tends to be high. In consequence, a space for the lenses and the view-direction changing element P cannot be provided, or a large angle of view cannot be achieved.

If the value of FL1/FLf falls below the lower limit value of conditional expression (2), the refractive power of the front lens group GF is too low. This will break the balance of the retro focus configuration. In consequence, a sufficient space for focus adjustment cannot be left.

In a preferred mode of the embodiment, it is desirable that the following conditional expressions (3) and (4) be satisfied:

$$-95 < (r2f+r2r)/(r2f-r2r) < -18 \tag{3}$$

$$2.8 < FLr/FL < 4 \tag{4}$$

where r2f is the curvature radius of the object side surface of the meniscus second lens L2, r2r is the curvature radius of the image side surface of the meniscus second lens L2, and FLr is the focal length of the rear lens group GR.

Conditional expression (3) defines the shape factor of the meniscus second lens L2. If conditional expression (3) is satisfied, it is possible to control the ray height by the meniscus second lens L2 to provide a space for the view-direction changing element P and the lenses disposed on the image side of the view-direction changing element P.

Moreover, chromatic aberration of magnification and distortion generated by the negative first lens L1 can be corrected satisfactorily by the meniscus second lens L2. Satisfying conditional expression (3) is contributive to downsizing of the objective optical system 10 with respect to the radial direction.

Conditional expression (4) defines an appropriate range of the ratio of the focal length of the rear lens group GR and the focal length of the entire objective optical system 10. If conditional expression (4) is satisfied, the ray height in the rear lens group GF can be made low. Moreover, it is possible to provide a space for focus adjustment. Satisfying conditional expression (4) is contributive to downsizing of the objective optical system 10 with respect to the radial direction.

If the value of FLr/FL exceeds the upper limit value of conditional expression (4), the refractive power of the rear lens group GR is too low, leading to high ray height.

If the value of FLr/FL falls below the lower limit value of conditional expression (4), the refractive power of the rear lens group GR is too high, making it difficult to provide a sufficiently long back focus. The back focus is a space used for focus adjustment.

In a preferred mode of the embodiment, it is desirable that at least one of the following conditional expressions (5), (6), and (7) be satisfied:

$$0.25 < d23/FL2 < 5 \tag{5}$$

$$0.3 < df/FL2 < 0.7 \tag{6}$$

$$-1.2 < di/FLf < -0.7 \tag{7}$$

where d23 is the equivalent air distance from the image side surface of the meniscus second lens L2 to the surface of the rear lens group GR closest to the object, df is the equivalent air distance from the first lens L1 to the aperture stop S, di is the equivalent air distance from the lens in the rear lens group GR closest to the image to the image plane I, and FLf is the focal length of the front lens group GF.

Conditional expression (5) defines an appropriate range of the ratio of the equivalent air distance from the image side surface of the meniscus second lens L2 to the surface of the rear lens group GR closest to the object and the focal length of the meniscus second lens L2. Satisfying conditional expression (5) is contributive to downsizing of the objective optical system 10 with respect to the direction along the optical axis.

If the value of d23/FL2 exceeds the upper limit value of conditional expression (5), the space for view-angle changing element P is too large, making downsizing of the optical system difficult.

If the value of d23/FL2 falls below the lower limit value of conditional expression (5), the refractive power of the meniscus second lens L2 is too low. Then, correction of distortion and chromatic aberration of magnification will be insufficient, or it will be difficult to provide a space for the view-angle changing element P.

Conditional expression (6) defines an appropriate range of the ratio of the equivalent air distance from the first lens L1 to the aperture stop S and the focal length of the meniscus second lens L2.

If the value of df/FL2 exceeds the upper limit value of the conditional expression (6), the length of the front lens group GF is too long, making downsizing of the optical system difficult. Satisfying conditional expression (6) is contributive to downsizing of the objective optical system 10 with respect to the direction along the optical axis.

If the value of df/FL2 falls below the lower limit value of conditional expression (6), the refractive power of the meniscus second lens L2 is too low. Then, correction of distortion and chromatic aberration of magnification will be insufficient, or it will be difficult to provide a space for the lenses in the front lens group GF.

Conditional expression (7) defines an appropriate range of the ratio of the equivalent air distance from the lens in the rear lens group GR closest to the image to the image plane I and the focal length of the front lens group GF. Satisfying conditional expression (7) is contributive to downsizing of the objective optical system 10 with respect to the direction along the optical axis.

If the value of di/FLf exceeds the upper limit value of conditional expression (7), the negative refractive power of the front lens group GF is insufficient. Then, a sufficient space for focus adjustment cannot be provided.

If the value of di/FLf falls below the lower limit value of conditional expression (7), the negative refractive power of the front lens group GF is too high, making the space for focus adjustment large. This makes downsizing of the objective optical system 10 difficult.

In a preferred mode of the embodiment, it is desirable that the positive rear lens group GR include a first positive third lens L3 and a cemented lens CL made up of a second positive fourth lens L4 and a negative fifth lens L5, and the following conditional expression (8) be satisfied:

$$1.25 < FLe4/FLe3 < 5 \qquad (8)$$

where FLe3 is the focal length of the first positive third lens L3, and FLe4 is the focal length of the cemented lens CL.

Conditional expression (8) defines an appropriate range of the ratio of the focal length of the positive third lens L3 and the focal length of the cemented lens CL. Satisfying conditional expression (8) is contributive to downsizing of the objective optical system 10 with respect to the radial direction.

If the value of FLe4/FLe3 falls below the lower limit value of conditional expression (8), the refractive power of the positive third lens L3 is so low that correction of spherical aberration and coma will be insufficient. Moreover, the ray height becomes high in the region before (namely, on the object side of) the cemented lens CL, leading to difficulties in downsizing the diameter of the optical system.

If the value of FLe4/FLe3 exceeds the upper limit value of conditional expression (8), the refractive power of the cemented lens CL is too low. Then, correction of chromatic aberration will be insufficient. Moreover, the image height is made high. This is undesirable for downsizing of the image pickup element.

In a preferred mode of the embodiment, it is desirable that the following conditional expression (9) be satisfied:

$$-1.5 < r5r/FLr < 0 \qquad (9)$$

where r5r is the curvature radius of the surface in the rear lens group GR closest to the image.

Conditional expression (9) defines an appropriate range of the ratio of the curvature radius of the surface in the rear lens group GR closest to the image and the focal length of the rear lens group GR. Satisfying conditional expression (9) is contributive to downsizing of the objective optical system 10 with respect to the direction along the optical axis.

IF the value of r5r/FLr exceeds the upper limit value of conditional expression (9), it is difficult to provide a sufficiently long back focus, which is a space used for focus adjustment in the assembly process.

If the value of r5r/FLr falls below the lower limit value of conditional expression (9), the refractive power of the rear lens group GF is too low, or the refractive power of the cemented lens CL is too low. In the former case, correction of spherical aberration and coma will be insufficient. In the latter case, the space for focus adjustment will be large, which is undesirable for downsizing of the optical system.

Second Embodiment

Figure 6:
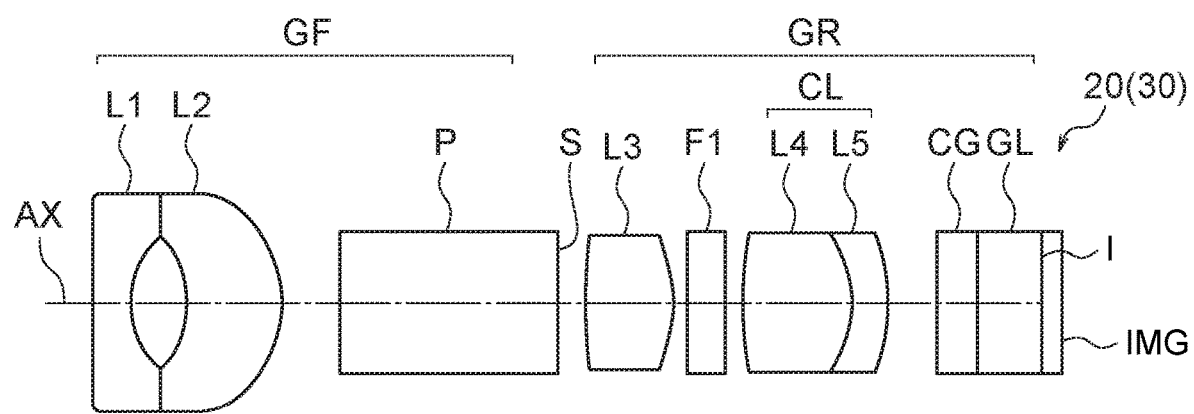
FIG. 6 is a cross sectional view of an image pickup apparatus according to a second embodiment and an endoscope according to a third embodiment.

FIG. 6 is a cross sectional view of an image pickup apparatus 20 according to a second embodiment. The image pickup apparatus 20 according to the second embodiment includes an objective optical system 10 and an image pickup element IMG. The objective optical system 10 used in this image pickup apparatus is the above-described objective optical system 10 according to the first embodiment.

The image pickup apparatus 20 of this embodiment is small in size and easy to assemble.

Third Embodiment

FIG. 6 is a cross sectional view of an endoscope according to a third embodiment. The endoscope 30 according to the third embodiment includes an objective optical system 10 and an image pickup element IMG. The objective optical system 10 used in this endoscope is the above-described objective optical system 10 according to the first embodiment.

The endoscope 30 of this embodiment is small in size and easy to assemble.

In the following, examples will be described.

Example 1

Figure 2A:
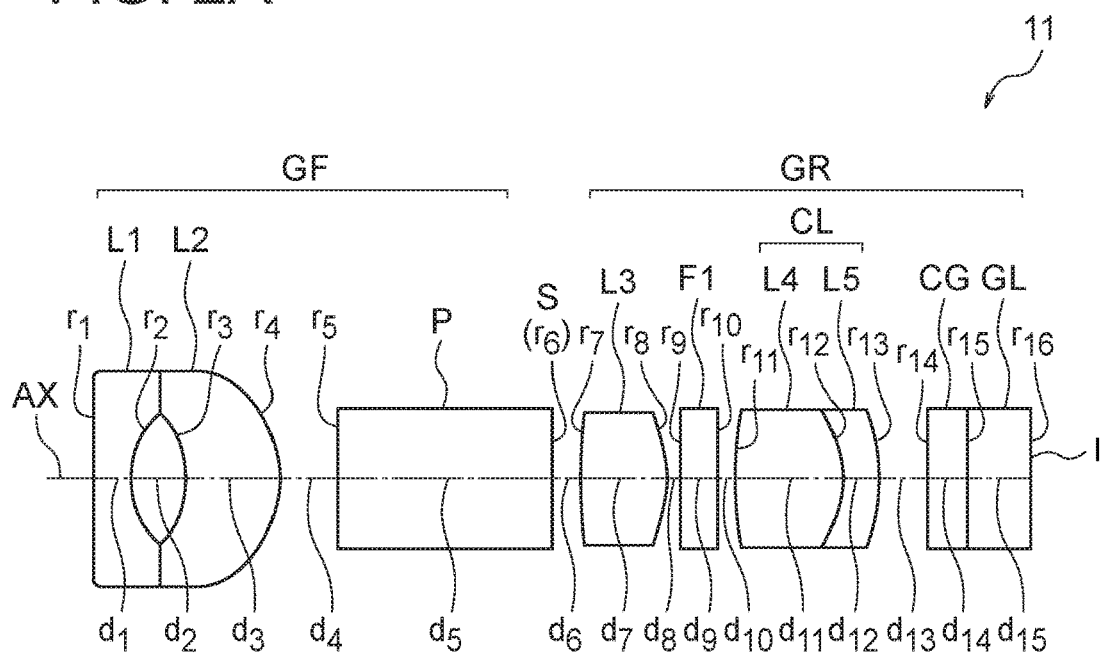
FIG. 2A is a cross sectional view of the lenses in an objective optical system of example 1.
Figures 2B, 2C, 2D, 2E:
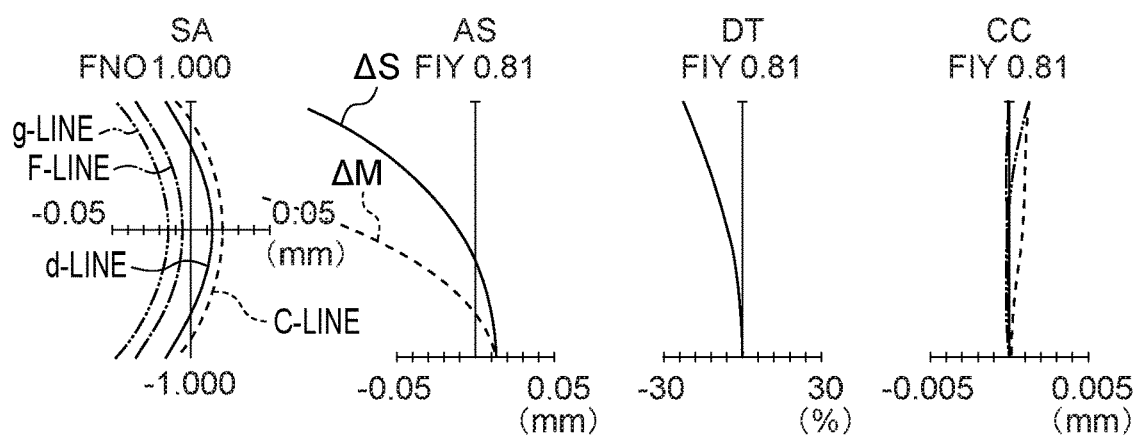
FIGS. 2B, 2C, 2D, and 2E are diagrams showing aberrations of the objective optical system of example 1.

FIG. 2A is a cross sectional view of the lenses in an objective optical system 11 of example 1.

The objective optical system 11 of this example includes, in order from the object side to the image side, a negative front lens group GF, an aperture stop S, and a positive rear lens group GR.

The front lens group GF includes a negative planoconcave first lens L1 having a flat surface facing toward the object side and disposed closest to the object, a negative meniscus second lens L2 having a convex surface facing toward the image side, and a view-direction changing element P. The rear lens group GR includes, a positive biconvex third lens L3, a plane parallel plate F1, a positive biconvex fourth lens L4, a negative meniscus fifth lens L5 having a convex surface facing toward the image side, a cover glass CG, and a glass lid GL.

The aperture stop S is disposed between the front lens group GF and the rear lens group Gr. The aperture stop S in the optical system of this example is provided on the image side surface of the view-direction changing element P.

The plane parallel plate F1 is an infrared cut filter. In FIG. 2A, what is denoted by I is the image plane.

The positive fourth lens L4 and the negative meniscus fifth lens L5 are cemented together to constitute a cemented lens CL. The cover glass CG and the glass lid GL are cemented together.

FIGS. 2B, 2C, 2D, and 2E respectively show spherical aberration (SA), astigmatism (AS), distortion (DT), and chromatic aberration of magnification (CC) of the optical system of this example. In these aberration diagrams, FIY denotes the image height.

Example 2

Figure 3A:
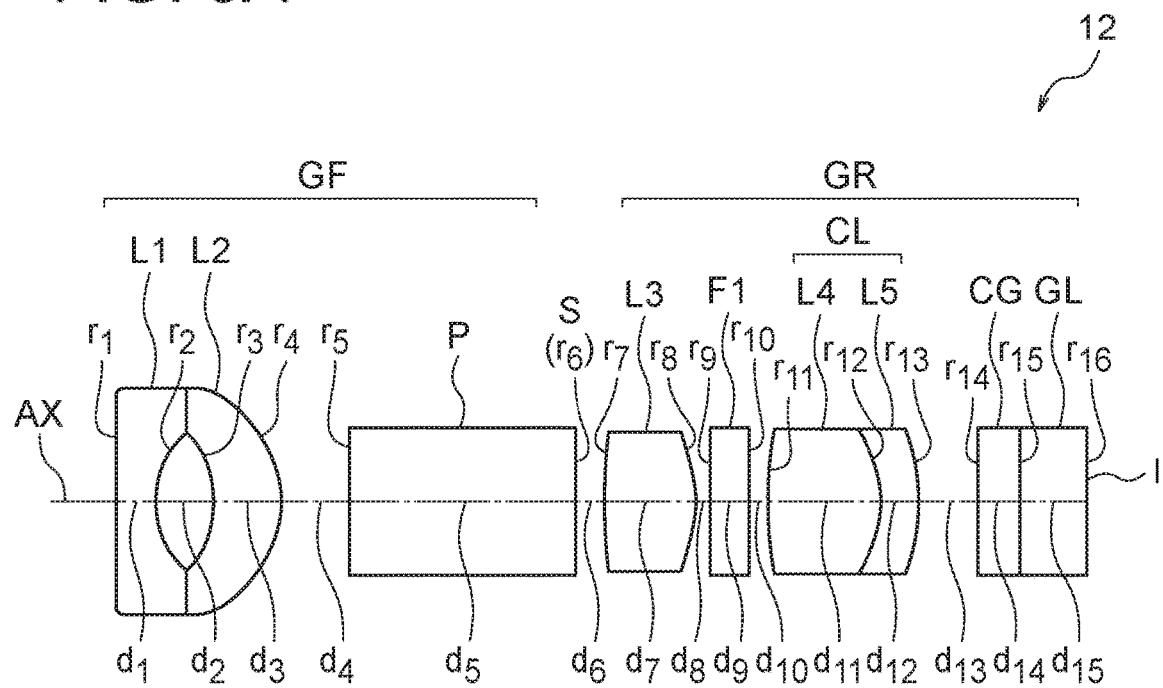
FIG. 3A is a cross sectional view of the lenses in an objective optical system of example 2.
Figures 3B, 3C, 3D, 3E:
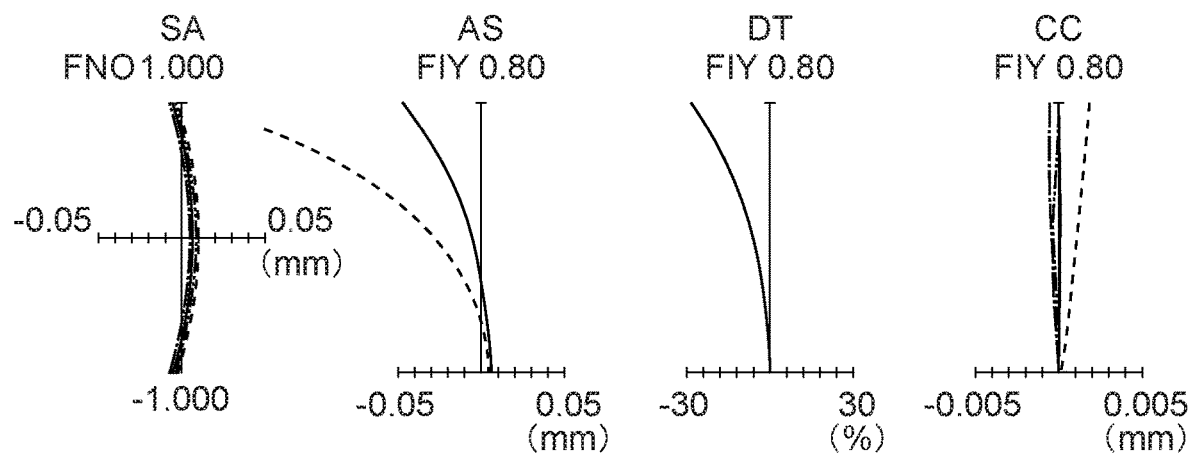
FIGS. 3B, 3C, 3D, and 3E are diagrams showing aberrations of the objective optical system of example 2.

FIG. 3A is a cross sectional view of the lenses in an objective optical system 12 of example 2.

The objective optical system 12 of this example includes, in order from the object side to the image side, a negative front lens group GF, an aperture stop S, and a positive rear lens group GR.

The front lens group GF includes a negative planoconcave first lens L1 having a flat surface facing toward the object side and disposed closest to the object, a negative meniscus second lens L2 having a convex surface facing toward the image side, and a view-direction changing element P. The rear lens group GR includes, a positive biconvex third lens L3, a plane parallel plate F1, a positive biconvex fourth lens L4, a negative meniscus fifth lens L5 having a convex surface facing toward the image side, a cover glass CG, and a glass lid GL.

The aperture stop S is disposed between the front lens group GF and the rear lens group Gr. The aperture stop S in the optical system of this example is provided on the image side surface of the view-direction changing element P.

The plane parallel plate F1 is an infrared cut filter. In FIG. 3A, what is denoted by I is the image plane.

The positive fourth lens L4 and the negative meniscus fifth lens L5 are cemented together to constitute a cemented lens CL. The cover glass CG and the glass lid GL are cemented together.

FIGS. 3B, 3C, 3D, and 3E respectively show spherical aberration (SA), astigmatism (AS), distortion (DT), and chromatic aberration of magnification (CC) of the optical system of this example. In these aberration diagrams, FIY denotes the image height.

Example 3

Figure 4A:
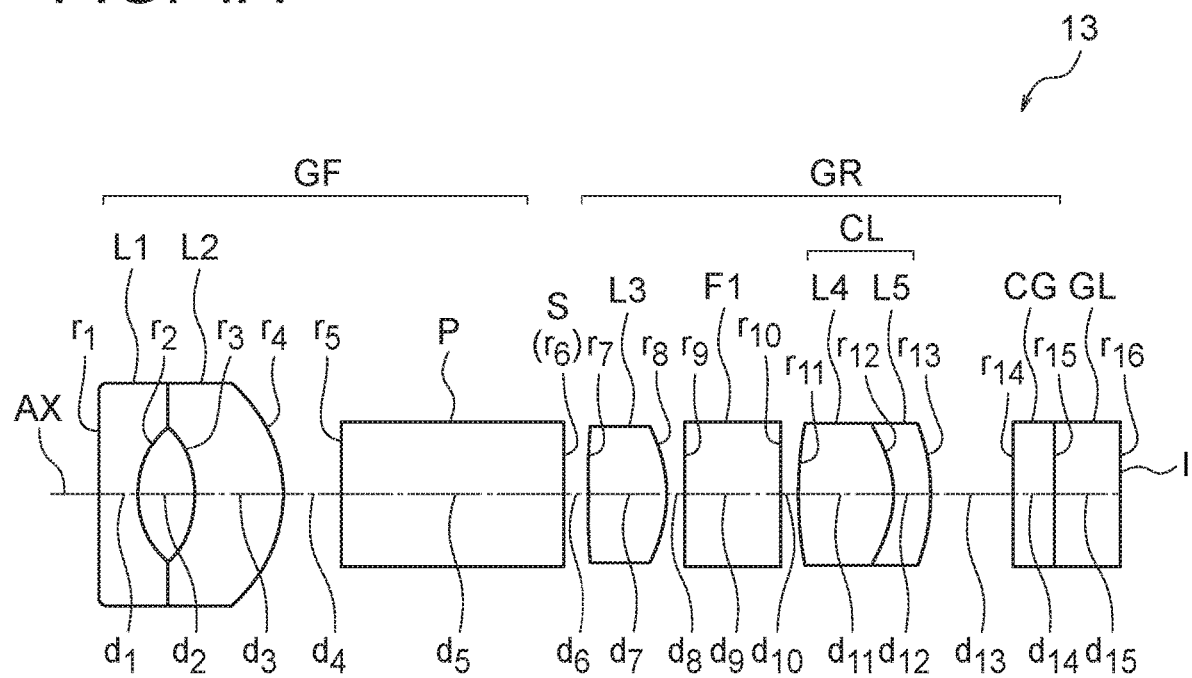
FIG. 4A is a cross sectional view of the lenses in an objective optical system of example 3.
Figures 4B, 4C, 4D, 4E:
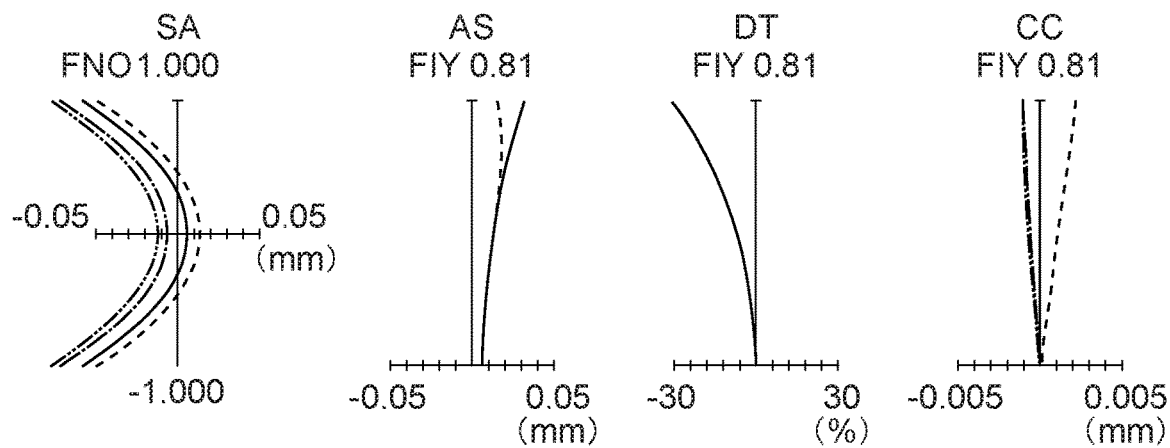
FIGS. 4B, 4C, 4D, and 4E are diagrams showing aberrations of the objective optical system of example 3.

FIG. 4A is a cross sectional view of the lenses in an objective optical system 13 of example 3.

The objective optical system 13 of this example includes, in order from the object side to the image side, a negative front lens group GF, an aperture stop S, and a positive rear lens group GR.

The front lens group GF includes a negative planoconcave first lens L1 having a flat surface facing toward the object side and disposed closest to the object, a negative meniscus second lens L2 having a convex surface facing toward the image side, and a view-direction changing element P. The rear lens group GR includes, a positive biconvex third lens L3, a plane parallel plate F1, a positive biconvex fourth lens L4, a negative meniscus fifth lens L5 having a convex surface facing toward the image side, a cover glass CG, and a glass lid GL.

The aperture stop S is disposed between the front lens group GF and the rear lens group Gr. The aperture stop S in the optical system of this example is provided on the image side surface of the view-direction changing element P.

The plane parallel plate F1 is an infrared cut filter. In FIG. 4A, what is denoted by I is the image plane.

The positive fourth lens L4 and the negative meniscus fifth lens L5 are cemented together to constitute a cemented lens CL. The cover glass CG and the glass lid GL are cemented together.

FIGS. 4B, 4C, 4D, and 4E respectively show spherical aberration (SA), astigmatism (AS), distortion (DT), and chromatic aberration of magnification (CC) of the optical system of this example. In these aberration diagrams, FIY denotes the image height.

Example 4

Figure 5A:
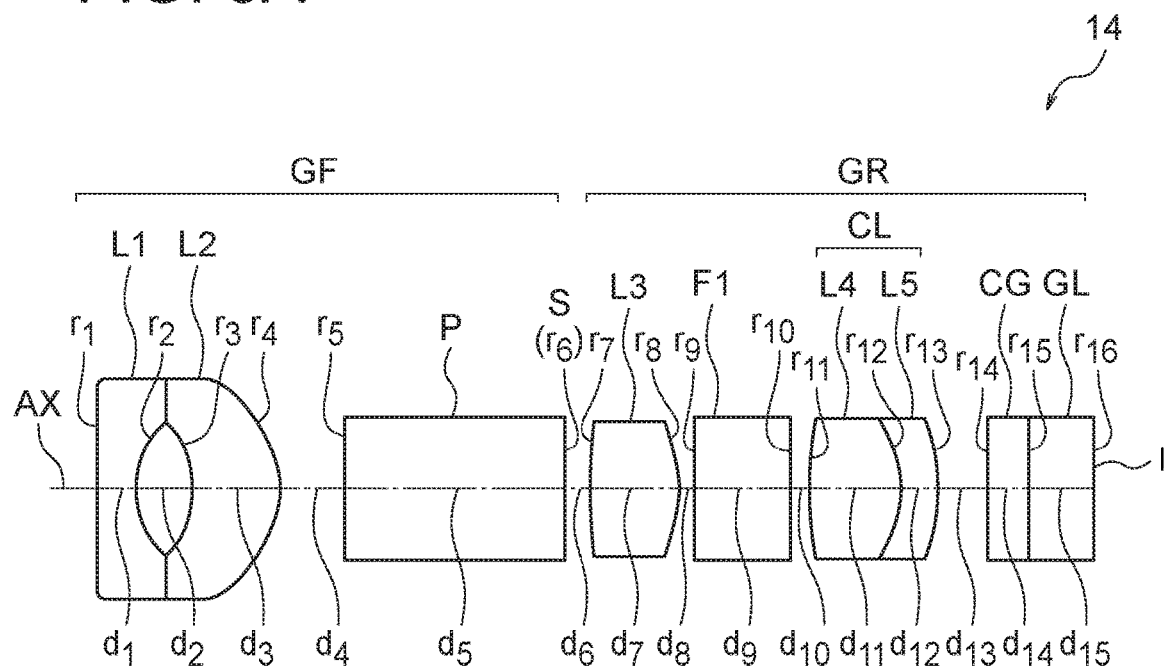
FIG. 5A is a cross sectional view of the lenses in an objective optical system of example 4.
Figures 5B, 5C, 5D, 5E:
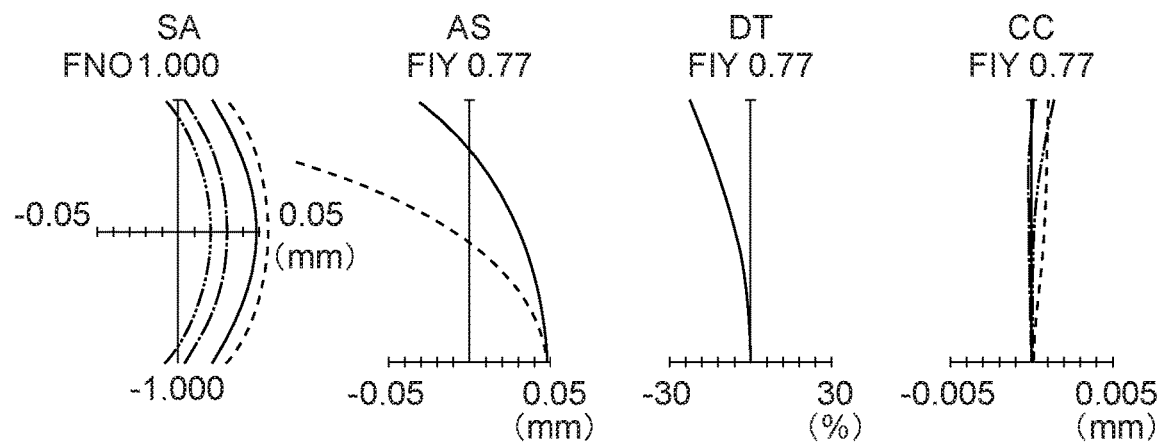
FIGS. 5B, 5C, 5D, and 5E are diagrams showing aberrations of the objective optical system of example 4.

FIG. 5A is a cross sectional view of the lenses in an objective optical system 14 of example 4.

The objective optical system 14 of this example includes, in order from the object side to the image side, a negative front lens group GF, an aperture stop S, and a positive rear lens group GR.

The front lens group GF includes a negative planoconcave first lens L1 having a flat surface facing toward the object side and disposed closest to the object, a negative meniscus second lens L2 having a convex surface facing toward the image side, and a view-direction changing element P. The rear lens group GR includes, a positive biconvex third lens L3, a plane parallel plate F1, a positive biconvex fourth lens L4, a negative meniscus fifth lens L5 having a convex surface facing toward the image side, a cover glass CG, and a glass lid GL.

The aperture stop S is disposed between the front lens group GF and the rear lens group Gr. The aperture stop S in the optical system of this example is provided on the image side surface of the view-direction changing element P.

The plane parallel plate F1 is an infrared cut filter. In FIG. 5A, what is denoted by I is the image plane.

The positive fourth lens L4 and the negative meniscus fifth lens L5 are cemented together to constitute a cemented lens CL. The cover glass CG and the glass lid GL are cemented together.

FIGS. 5B, 5C, 5D, and 5E respectively show spherical aberration (SA), astigmatism (AS), distortion (DT), and chromatic aberration of magnification (CC) of the optical system of this example. In these aberration diagrams, FIY denotes the image height.

In the following, numerical data of the above-described examples will be given. In the surface data, r is the radius of curvature of each surface, d is the distance between adjacent lens surfaces, nd is the refractive index of each lens at d-line, and vd is the Abbe number of each lens. The term "stop" refers to the aperture stop in each example.

Example 1

Unit mm
Surface data

| Surface no. | r | d | nd | vd |
|---|---|---|---|---|
| 1 | ∞ | 0.5344 | 1.882997 | 40.76 |
| 2 | 1.4832 | 0.8194 | | |
| 3 | −1.6201 | 1.3944 | 1.717362 | 29.52 |
| 4 | −1.7841 | 0.8372 | | |
| 5 | ∞ | 3.2062 | 1.882997 | 40.76 |
| 6 (Stop) | ∞ | 0.3919 | | |
| 7 | 7.4745 | 1.2468 | 1.48749 | 70.23 |
| 8 | −2.5512 | 0.2316 | | |
| 9 | ∞ | 0.5344 | 1.49557 | 75 |
| 10 | ∞ | 0.2316 | | |
| 11 | 4.2858 | 1.6031 | 1.51633 | 64.14 |
| 12 | −1.7117 | 0.5344 | 1.92286 | 18.9 |
| 13 | −3.0991 | 0.7089 | | |
| 14 | ∞ | 0.5878 | 1.51633 | 64.14 |
| 15 | ∞ | 0.8906 | 1.507 | 63.26 |
| 16 | ∞ | 0.0089 | | |
| Image pickup surface | ∞ | 0 | | |

Example 2

Unit mm
Surface data

| Surface no. | r | d | nd | vd |
|---|---|---|---|---|
| 1 | ∞ | 0.5282 | 1.882997 | 40.76 |
| 2 | 1.4384 | 0.8099 | | |
| 3 | −1.7653 | 0.8803 | 1.717362 | 29.52 |
| 4 | −1.8357 | 0.9507 | | |
| 5 | ∞ | 3.1691 | 1.882997 | 40.76 |
| 6 (Stop) | ∞ | 0.3873 | | |
| 7 | 4.2554 | 1.2324 | 1.48749 | 70.23 |
| 8 | −3.4103 | 0.2289 | | |
| 9 | ∞ | 0.5282 | 1.49557 | 75 |
| 10 | ∞ | 0.2289 | | |
| 11 | 3.199 | 1.5845 | 1.51633 | 64.14 |
| 12 | −1.5388 | 0.5282 | 1.92286 | 18.9 |
| 13 | −2.9349 | 0.8965 | | |
| 14 | ∞ | 0.581 | 1.51633 | 64.14 |
| 15 | ∞ | 0.8803 | 1.507 | |
| 17 | ∞ | 0.0088 | 1 | |
| Image pickup surface | ∞ | 0 | | |

Example 3

Unit mm
Surface data

| Surface no. | r | d | nd | vd |
|---|---|---|---|---|
| 1 | ∞ | 0.5336 | 1.882997 | 40.76 |
| 2 | 1.2387 | 0.8183 | | |
| 3 | −2.0296 | 1.3389 | 1.717362 | 29.52 |
| 4 | −2.1013 | 0.8851 | | |
| 5 | ∞ | 3.2019 | 1.882997 | 40.76 |
| 6 (Stop) | ∞ | 0.3913 | | |
| 7 | 20.5799 | 1.1651 | 1.48749 | 70.23 |
| 8 | −2.1729 | 0.2312 | | |
| 9 | ∞ | 1.4231 | 1.49557 | 75 |
| 10 | ∞ | 0.2312 | | |
| 11 | 5.6371 | 1.4092 | 1.51633 | 64.14 |
| 12 | −1.8351 | 0.5336 | 1.92286 | 18.9 |
| 13 | −3.2363 | 1.2721 | | |
| 14 | ∞ | 0.587 | 1.51633 | 64.14 |
| 15 | ∞ | 0.8894 | 1.507 | 63.26 |
| 16 | ∞ | 0.0089 | | |
| Image pickup surface | ∞ | 0 | | |

Example 4

Unit mm
Surface data

| Surface no. | r | d | nd | vd |
|---|---|---|---|---|
| 1 | ∞ | 0.5079 | 1.882997 | 40.76 |
| 2 | 1.3143 | 0.7787 | | |
| 3 | −1.6415 | 1.2284 | 1.717362 | 29.52 |
| 4 | −1.7226 | 0.8535 | | |
| 5 | ∞ | 3.0471 | 1.882997 | 40.76 |
| 6 (Stop) | ∞ | 0.3724 | | |
| 7 | 6.4323 | 1.1847 | 1.48749 | 70.23 |
| 8 | −2.5561 | 0.2201 | | |
| 9 | ∞ | 1.3543 | 1.49557 | 75 |
| 10 | ∞ | 0.2201 | | |
| 11 | 3.9566 | 1.2573 | 1.51633 | 64.14 |
| 12 | −1.6339 | 0.5079 | 1.92286 | 18.9 |
| 13 | −2.962 | 0.7156 | | |
| 14 | ∞ | 0.5586 | 1.51633 | 64.14 |
| 15 | ∞ | 0.8464 | 1.507 | 63.26 |
| 16 | ∞ | 0.0085 | | |
| Image pickup surface | ∞ | 0 | | |

The corresponding values of the conditional expressions for each example are shown below.

$$FL2/FL \tag{1}$$

$$FL1/FLf \tag{2}$$

$$(r2f+r2r)/(r2f-r2r) \tag{3}$$

$$FLr/FL \tag{4}$$

$$d23/FL2 \tag{5}$$

$$df/FL2 \tag{6}$$

$$di/FLf \tag{7}$$

$$FLe4/FLe3 \tag{8}$$

$$r5r/fr \tag{9}$$

| Conditional expression | | | | |
|---|---|---|---|---|
| | Example1 | Example2 | Example3 | Example4 |
| (1) | 9.49 | 14.99 | 12.03 | 9.00 |
| (2) | 0.41 | 0.64 | 0.55 | 0.45 |
| (3) | −20.75 | −51.17 | −57.67 | −41.50 |
| (4) | 2.95 | 2.84 | 3.25 | 3.01 |
| (5) | 0.31 | 0.20 | 0.25 | 0.32 |
| (6) | 0.29 | 0.17 | 0.23 | 0.29 |
| (7) | −0.49 | −0.86 | −1.01 | −0.59 |
| (8) | 0.73 | 0.85 | 0.64 | 0.75 |
| (9) | −1.05 | −1.03 | −0.99 | −0.98 |

Two or more features of the above-described objective optical systems may be employed in combination. To provide an objective optical system having good performance, it is preferred to employ two or more features. The numerical ranges limited by the conditional expressions given above may be further limited. In this connection, both or only one of the upper and lower limit values may be further limited.

While various embodiments of the present invention have been described, the present invention is not limited to the embodiments. Other embodiments that employ features of the above-described embodiments in combination will also fall within the scope of the present invention, so long as they do not depart from the essence of the present invention.

As above, the present invention can suitably be applied to objective optical systems, image pickup apparatuses, and endoscopes that are required to be small in size and easy to assemble.

The present invention can provide an objective optical system, an image pickup apparatus, and an endoscope that are small in size and easy to assemble.

What is claimed is:

1. An objective optical system comprising, in order from the object side to the image side:
   a negative front lens group;
   an aperture stop; and
   a positive rear lens group,
wherein the front lens group includes a negative first lens disposed closest to the object, a meniscus second lens having a convex surface facing toward the image side, and a view-direction changing element, and the objective optical system satisfies the following conditional expressions (1) to (4):

$$9 < FL2/FL < 15 \quad (1)$$

$$0.3 < FL1/FLf < 0.64 \quad (2)$$

$$-95 < (r2f + r2r)/(r2f - r2r) < -18 \quad (3)$$

$$2.8 < FLr/FL < 4 \quad (4)$$

where FL1 is the focal length of the first lens, FL2 is the focal length of the meniscus second lens, FLf is the focal length of the front lens group, FL is the focal length of the entire objective optical system, r2f is the curvature radius of the object side surface of the meniscus second lens, r2r is the curvature radius of the image side surface of the meniscus second lens, and FLr is the focal length of the rear lens group.

2. An objective optical system according to claim 1, wherein the objective optical system satisfies at least one of the following conditional expressions (5), (6), and (7):

$$0.25 < d23/FL2 < 5 \quad (5)$$

$$0.3 < df/FL2 < 0.7 \quad (6)$$

$$-1.2 < di/FLf < -0.7 \quad (7)$$

where d23 is the equivalent air distance from the image side surface of the meniscus second lens to the surface of the rear lens group closest to the object, df is the equivalent air distance from the first lens to the aperture stop, di is the equivalent air distance from the lens in the rear lens group closest to the image to the image plane, and FLf is the focal length of the front lens group.

3. An objective optical system according to claim 1, wherein the rear lens group comprises a first positive lens and a cemented lens made up of a second positive lens and a negative lens, and the objective optical system satisfies the following conditional expression (8):

$$1.25 < FLe4/FLe3 < 5 \quad (8)$$

where FLe3 is the focal length of the first positive lens, and FLe4 is the focal length of the cemented lens.

4. An objective optical system according to claim 1, wherein the objective optical system satisfies the following conditional expression (9):

$$-1.5 < r5r/FLr < 0 \quad (9)$$

where r5r is the curvature radius of the surface in the rear lens group closest to the image.

5. An image pickup apparatus comprising:
   an objective optical system; and
   an image pickup element,
wherein the objective optical system includes, in order from the object side to the image side, a negative front lens group, an aperture stop, and a positive rear lens group, the front lens group including a negative first lens disposed closest to the object, a meniscus second lens having a convex surface facing toward the image side, and a view-direction changing element, and the objective optical system satisfies the following conditional expressions (1) to (4):

$$9 < FL2/FL < 15 \quad (1)$$

$$0.3 < FL1/FLf < 0.64 \quad (2)$$

$$-95 < (r2f + r2r)/(r2f - r2r) < -18 \quad (3)$$

$$2.8 < FLr/FL < 4 \quad (4)$$

6. An endoscope comprising:
   an objective optical system; and
   an image pickup element,
wherein the objective optical system includes, in order from the object side to the image side, a negative front lens group, an aperture stop, and a positive rear lens group, the front lens group including a negative first lens disposed closest to the object, a meniscus second lens having a convex surface facing toward the image side, and a view-direction changing element, and the objective optical system satisfies the following conditional expressions (1) to (4):

$$9 < FL2/FL < 15 \quad (1)$$

$$0.3 < FL1/FLf < 0.64 \quad (2)$$

$$-95 < (r2f + r2r)/(r2f - r2r) < -18 \quad (3)$$

$$2.8 < FLr/FL < 4 \quad (4)$$

where FL1 is the focal length of the first lens, FL2 is the focal length of the meniscus second lens, FLf is the focal length of the front lens group, FL is the focal length of the entire objective optical system, r2f is the curvature radius of the object side surface of the meniscus second lens, r2r is the curvature radius of the image side surface of the meniscus second lens, and FLr is the focal length of the rear lens group.

* * * * *